United States Patent [19]

Partney, Jr.

[11] Patent Number: 5,350,510
[45] Date of Patent: Sep. 27, 1994

[54] APPARATUS FOR THIN LAYER CHROMATOGRAPHY

[75] Inventor: Donald W. Partney, Jr., Granite City, Ill.

[73] Assignee: Granite Engineering, Inc., Granite City, Ill.

[21] Appl. No.: 16,789

[22] Filed: Feb. 11, 1993

[51] Int. Cl.$^5$ ............................................. B01D 15/08
[52] U.S. Cl. .................................. 210/198.3; 210/658; 73/61.54
[58] Field of Search ............... 210/658, 198.3; 422/70; 436/162, 178; 73/61.54

[56] References Cited

U.S. PATENT DOCUMENTS

| | | | |
|---|---|---|---|
| T.986,008 | 9/1979 | Gordon | 210/198.3 |
| 3,067,132 | 12/1962 | Gunew | 210/198.3 |
| 3,189,541 | 6/1965 | Brenner et al. | 210/658 |
| 3,318,451 | 5/1967 | Przybylowicz et al. | 210/658 |
| 3,342,333 | 9/1967 | Geiss | 210/198.3 |
| 3,375,929 | 4/1968 | Jeffreys et al. | 210/658 |
| 3,464,560 | 9/1969 | Clement et al. | 210/658 |
| 3,491,883 | 1/1970 | Schriftman | 210/198.3 |
| 3,623,602 | 11/1971 | Valente | 210/198.3 |
| 3,629,098 | 12/1971 | Hara | 210/198.3 |
| 3,752,316 | 8/1973 | Takeshita | 210/198.3 |
| 3,857,784 | 12/1974 | Martinez | 210/198.3 |
| 3,864,250 | 2/1975 | Perry | 210/198.3 |
| 3,915,856 | 10/1975 | Meyer | 210/658 |
| 3,963,421 | 6/1976 | Jones | 210/658 |
| 4,065,384 | 12/1977 | Pandey et al. | 210/658 |
| 4,272,381 | 6/1981 | Kremer et al. | 210/658 |
| 4,306,977 | 12/1981 | Pan | 210/658 |
| 4,377,641 | 3/1983 | Dee | 210/198.3 |
| 4,736,538 | 4/1988 | Pierce et al. | 40/158 B |
| 4,986,909 | 1/1991 | Rai | 210/198.3 |
| 4,999,285 | 3/1991 | Stiso | 210/198.3 |

FOREIGN PATENT DOCUMENTS 1469453 3/1989 U.S.S.R. ............................. 73/61.54

OTHER PUBLICATIONS

P. E. Flinn, A. S. Kenyon, and T. P. Layloff; "A Simplified TLC System For Qualitative And Semi-Qualitative Analysis Of Pharmaceuticals"; Journal of Liquid Chromatography 15(10) pp. 1639–1653; 1992.

P. E. Flinn, Y. H. Juhl, and T. P. Layloff; "A Simple, Inexpensive Thin-Layer Chromatography Method For The Analysis Of Theophylline Tablets"; Bulletin of the World Health Organization 67(5) pp. 555–559; 1989.

Primary Examiner—Ernest G. Therkorn
Attorney, Agent, or Firm—Rogers, Howell & Haferkamp

[57] ABSTRACT

An apparatus for use in the performance of thin layer chromatography of the type which utilizes a thin bag as the developing chamber for the chromatogram is provided. The apparatus has a pair of substantially identical frames which hold the bag between the frames in a manner sealing the upper and lower ends of the bag while permitting sliding movement of the bag vertically within the frame. The frames are connected by a hinge which permits pivoting of the frames between an open and a closed position. In the closed position, the inner surfaces of the frame are aligned in a face-to-face relationship which accommodates the placement of the chromatography bag between the frames and holds the bag in an upright manner by frictional engagement of the bag with the inner surface of the frame. The bag is sealed by the action of outwardly extending ribs or a resilient pad presented on the inner surface of at least one of the upper and lower crossmembers of the frames.

14 Claims, 2 Drawing Sheets

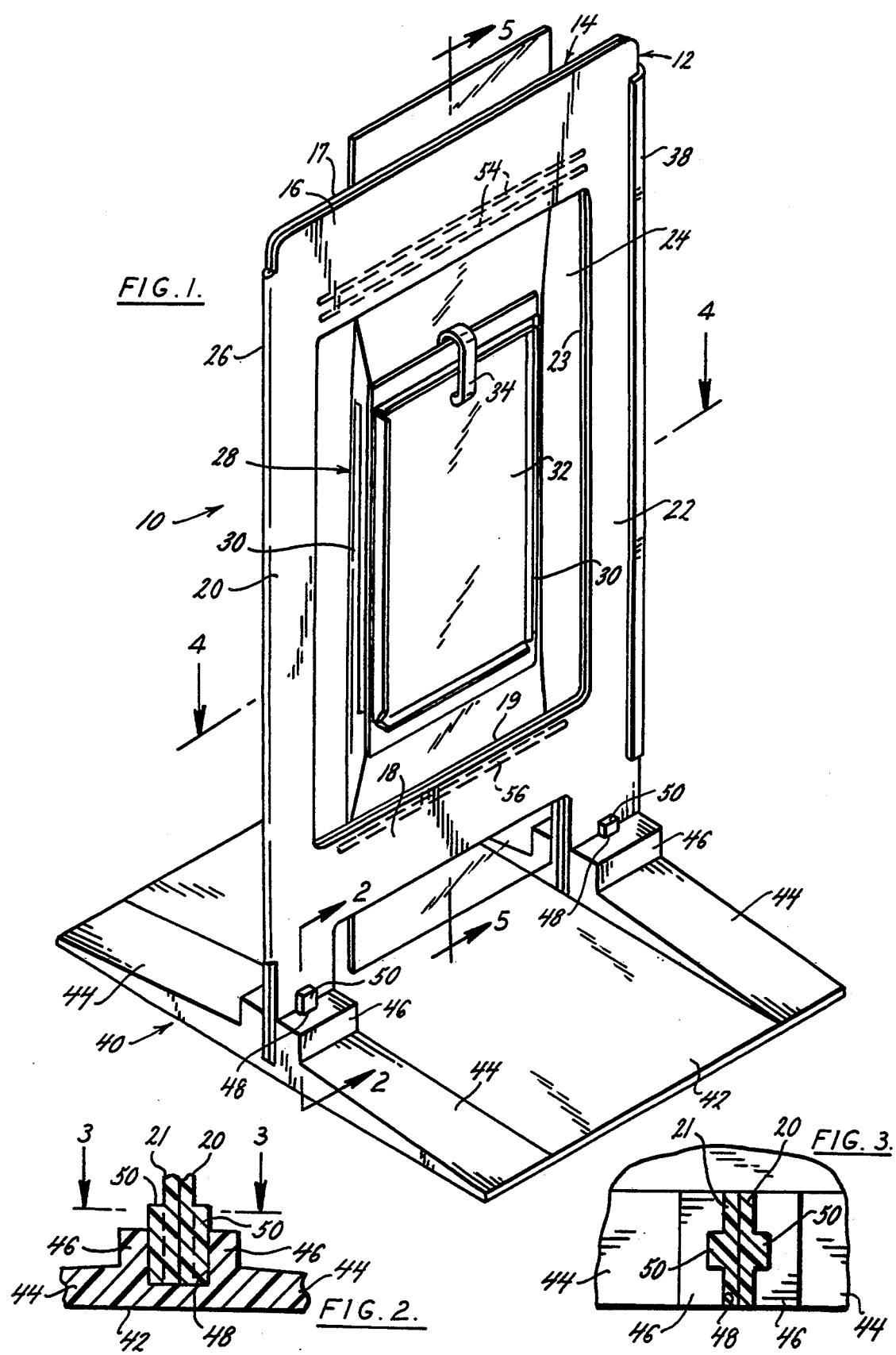

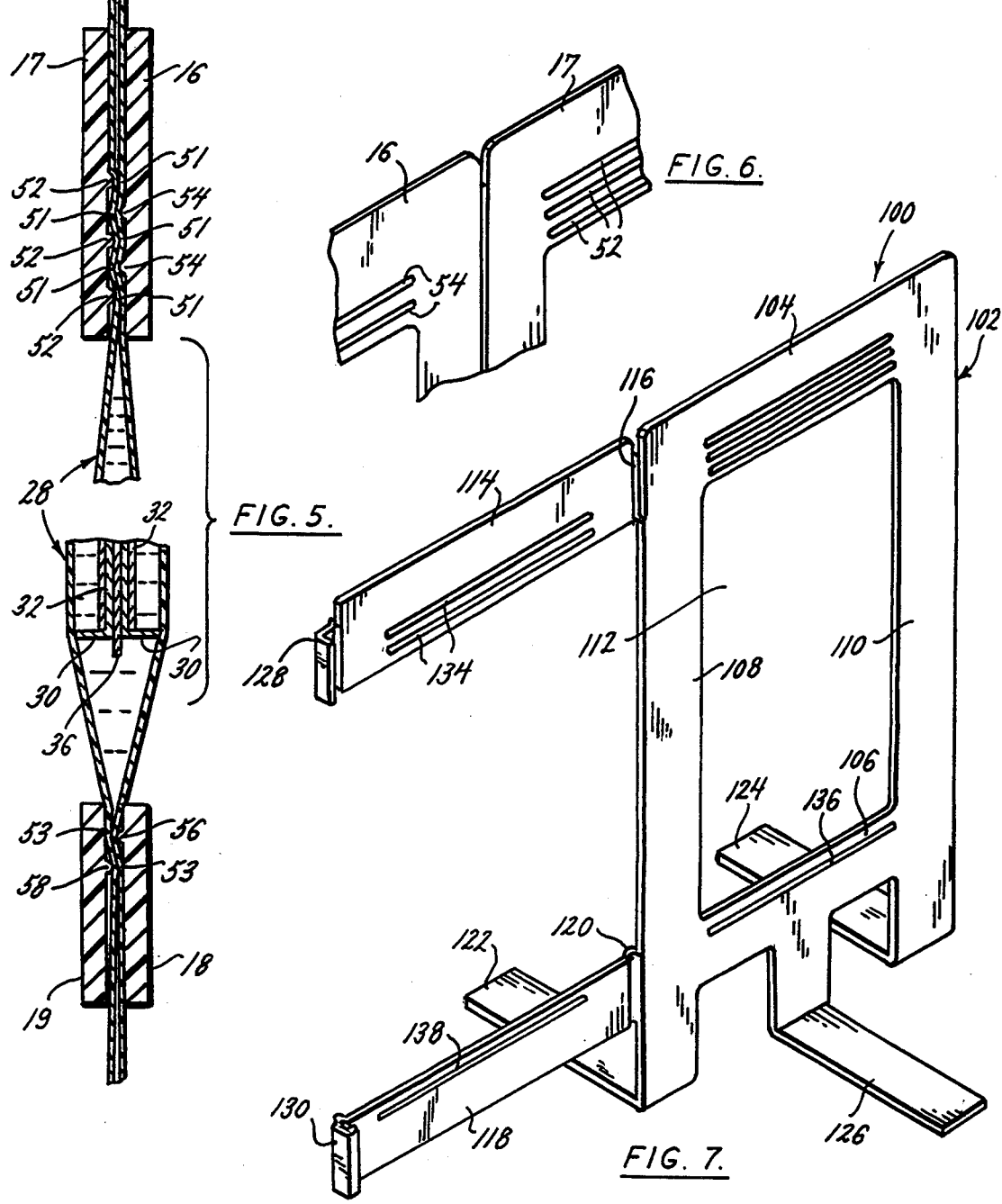

APPARATUS FOR THIN LAYER CHROMATOGRAPHY

BACKGROUND OF THE INVENTION

This invention relates in general to chromatography and, more particularly, to an apparatus useful in the performance of thin layer chromatography of the type conducted in a plastic bag or the like.

Thin layer chromatography is an analytical chemical procedure conducted in numerous laboratories for determining the identity of compounds in a solution. Briefly, a solution containing a chemical compound to be identified is applied near one end of a chromatography sheet and the end of the sheet is immersed in an elution solvent which selectively separates the chemical compounds in the solution. Conventionally, thin layer chromatography of this type is conducted in thick glass tanks where the solvent is placed in the bottom of the tank, the chromatography sheet inserted into the tank and the tank covered with a glass sheet to provide a sealed chromatographic chamber. Although this type of device has proved useful in conducting thin layer chromatography, it is disadvantageous because the glass tanks are heavy, easily broken and expensive. Moreover, the use of these heavy, glass developing chambers are not particularly suitable for use in a portable thin layer chromatography system.

Thin layer chromatography has also been conducted in free-standing plastic sleeves. These sleeves are formed of a sturdy and semi-rigid plastic material and are closed at one end and open at the opposite end. The developing solution is inserted into the sleeve and the chromatographic sheet inserted into the solution. The sleeve is typically sealed by folding the top of the sleeve and attaching a clamp to the folded over portion of the sleeve. One disadvantage of this type of chromatographic chamber is that it is difficult to pre-equilibrate the atmosphere in the chamber before beginning the development of the chromatogram. A better and more accurate chromatogram is obtained if the atmosphere in the chamber is equilibrated with the vapors of the solvent before the chromatogram development is initiated. Moreover, the rigid plastic sleeves are expensive and not suitable for applications where numerous assays are being conducted.

A simple, portable, and inexpensive thin layer chromatography method using thin polyethylene bags as the developing chamber for developing the chromatogram has also been described. Because such bags can not stand on their own, a support apparatus is required to conduct chromatographic analysis in thin plastic bags. Heretofore, support assemblies developed for use in the performance of thin layer chromatography using thin polyethylene bags are cumbersome, inefficient, do not provide an adequate means for sealing the bag to provide an air tight developing chamber and require the use of supplemental sealing devices exterior of the support apparatus.

There is, therefore, a need for a facile, efficient and effective support apparatus for use in the performance of thin layer chromatography using thin plastic bags which overcomes the foregoing problems.

SUMMARY OF THE INVENTION

The present invention provides an apparatus for use in the performance of thin-layer chromatography which utilizes a thin bag as the developing chamber for the chromatogram. In one embodiment, the apparatus comprises a pair of substantially identical frames, each frame having a pair of spaced apart, substantially vertical sidewalls and spaced apart, substantially horizontal upper and lower crossmembers which are arranged in a manner forming a central opening in each frame. The frames are connected between one of the sidewalls of each frame by a hinge which permits pivoting of the frames between an open and a closed position. In the closed position the inner surfaces of the frames are aligned in a face-to-face relationship which accommodates the placement of the chromatography bag between the frames and holds the bag in an upright manner by frictional engagement of the bag with the inner surface of the crossmembers. The upper and lower ends of a chromatography bag placed between the frames are sealed by the action of outwardly extending ribs presented on the inner surface of the upper and lower crossmembers of the frames. These ribs crimp the bag together and cause a plurality of folds in the bag which serve to seal the bag and create an airtight development chamber. In an alternate embodiment, a resilient pad formed of a compressible material is presented on the inner surface of at least one of the upper and lower crossmembers which serves to seal the bag by compression of the bag against the resilient pad and the other crossmember. Typically, a chromatography bag used in conjunction with the support apparatus of the present invention has at least one preformed seal at its lower end and the ribs presented in the lower crossmembers are used to force the developing solution in the bag into contact with the chromatographic sheet when the bag is pulled downwardly through the apparatus. Thus, although the ribs provide an airtight seal in the top and bottom of the bag, the bag can be moved vertically while held in the apparatus in the closed position. A latch is presented in connection with the frames to releasably maintain the frames in the closed position and a stand is provided to hold the frames in an upright manner when the frames are in the closed position.

In a second embodiment, an apparatus is provided having a frame with a pair of spaced apart, substantially vertical sidewalls and spaced apart, substantially horizontal upper and lower crossmembers arranged to form a central opening in the frame, an upper gate pivotably connected to the upper crossmember of the frame and a lower gate pivotably connected to the lower crossmember of the frame. The upper and lower gates are pivotable between an open position and a closed position wherein the inner surfaces of the upper and lower crossmembers and the inner surfaces of the corresponding upper and lower gates are substantially aligned in a face-to-face relationship when the upper and lower gates are in the closed position with respect to the frame. The inner surface of the gates and the crossmembers present ribs extending outwardly therefrom which serve to seal the upper and lower ends of a chromatography bag placed between the frame and the gates when in the closed position. The bag is sealed by the action of the ribs on the bag which cause the bag to crimp and produce folds in the bag. As previously described, a resilient pad formed of a compressible material could also be used to seal the bag. Although the ribs seal the bag, the bag remains capable of vertical movement in the apparatus. This embodiment also includes a latch connected to each gate to releasably maintain the gates in the closed position and a stand for holding the apparatus in an upright manner.

Among the many advantages of the present invention may be noted the provision of an apparatus useful in the performance of thin layer chromatography that is portable and inexpensive and that also facilitates the quick and efficient performance of thin layer chromatographic assays using thin plastic bags as the developing chamber; the provision of such an apparatus that incorporates a sealing means in the apparatus without the need for supplemental sealing devices; the provision of such an apparatus that is adapted to permit the pre-equilibration of the sealed developing chamber before initiating development of the chromatogram; and the provision of such an apparatus that is simple to operate.

Other and further advantages of the present invention will be made clear or become apparent from the following description of the invention taken in light of the drawing figures.

BRIEF DESCRIPTION OF THE DRAWINGS

FIG. 1 is a perspective view of one embodiment of an apparatus of this invention illustrating the apparatus in use and in the closed position;

FIG. 2 is an enlarged sectional view of the apparatus of FIG. 1 taken through the plane of the line 2—2 in FIG. 1;

FIG. 3 is an enlarged sectional view of the apparatus of FIG. 1 taken through the plane of the line 3—3 in FIG. 2;

FIG. 4 is a cross-sectional view of the apparatus of FIG. 1 taken through the plane of the line 4—4 in FIG. 1;

FIG. 5 is a fragmentary side sectional view of the apparatus of FIG. 1 taken through the plane of the line 5—5 in FIG. 1;

FIG. 6 is a fragmentary front elevational view of the apparatus of FIG. 1 illustrating the apparatus in its open position; and FIG. 7 is a perspective view of an alternate embodiment of the present invention.

DETAILED DESCRIPTION OF THE PREFERRED EMBODIMENTS

Referring initially to FIG. 1, one embodiment of an apparatus of the present invention is shown and designated generally by the numeral 10. The apparatus has a first frame 12 and a second frame 14. In this embodiment, the frames 12 and 14 are substantially identical. Frame 12 is formed having have an upper crossmember 16, a lower crossmember 18 and a pair of substantially vertical, spaced apart sidewalls 20 and 22. The frame 14 is formed by an upper crossmember 17, a lower crossmember 19, and a pair of substantially vertical, spaced apart sidewalls 21 and 23. Each of the frames 12 and 14 is formed in a manner providing a generally rectangular opening 24 therein. In an alternate embodiment (not shown), the frames could be formed generally in a "C" shape by elimination of one of the sidewalls.

Although the frames 12 and 14 could be formed as separate pieces, it is preferable to mold them together and connect them together with a hinge 26 along an outer edge of a sidewall of the frame. As shown in FIG. 1, a hinge 26 is shown along the outer edge of sidewall 20 of frame 12 and along the outer edge of the corresponding sidewall 21 in the frame 14. By connecting the frames 12 and 14 by the hinge 26, the frames can be pivoted between an open position and a closed position.

In the closed position, the inner surfaces of the frames 12 and 14 are aligned in a face-to-face relationship which permits a thin layer chromatography developing bag 28 to be positioned between the frames 12 and 14 and held therebetween as will be described hereinafter.

As shown in FIGS. 1 and 4, the frame 14 includes a pivoting latch 38 positioned along the outer edge of sidewall 23 to releasably maintain the frames 12 and 14 in a closed position. The latch 38 pivots to contact and engage the outer surface of the sidewall 22 of the frame 12 to securely hold the frames 12 and 14 together in the closed position. As is understood, the latch 38 could be presented along the edge of either frame 12 or 14 and other latching means for securing the inner surfaces of the frames together in a face-to-face relationship could be utilized.

The vertical sidewalls 20, 21, 22 and 23 of frames 12 and 14 extend below the respective lower crossmember 18 or 19 so that the sidewalls can be inserted into a stand 40 when the frames 12 and 14 are in the closed position. In addition, the placement of the lower crossmembers 18 and 19 above the lower edge of the sidewalls provides a space below the lower crossmembers 18 and 19 which permits the bag 28 inserted therebetween to be pulled downwardly through the frame as part of the chromatography procedure as will be discussed hereinafter.

As shown in FIGS. 1-3, stand 40 has a base 42 and four inclined surfaces 44 presented on the upper surface of the base 42 which terminate in a pair of central platforms 46. As best shown in FIG. 3, the platforms 46 include a notched groove 48 into which the lower portion of vertical sidewalls 20 and 21, and 22 and 23, when in the closed position, are inserted to hold the apparatus in an upright manner during the chromatographic procedure. Preferably, a rectangular lug 50 is provided on the outer surface of the vertical sidewalls 20, 21, 22 and 23 to provide a secure engagement of the sidewalls in the notched groove 48 in platform 46 of stand 40.

As shown in FIGS. 5 and 6, three spaced apart, generally horizontal ribs 52 are presented extending outwardly from the inner surface of the crossmember 17 and two similarly formed ribs 54 are presented extending outwardly from the inner surface of the crossmember 16. The purpose of the ribs 52 and 54 are to provide a seal in the upper end of the bag 28 when positioned between the crossmembers 16 and 17. When a bag 28 is placed between the frames 12 and 14, the bag is held in place in an upright position by the frictional engagement of the bag 28 with the inner surfaces of the crossmembers 16, 17, 18 and 19. The ribs 52 and 54 cause the sides of the bag to be pressed together to form folds 51 in the bag. This results in the bag being sealed in an airtight manner. As best shown in FIG. 5, the ribs 54 on the upper crossmember 16 are positioned for meshing engagement with the space between the ribs 52 of upper crossmember 17. This meshing engagement causes a plurality of folds 51 in the upper end of bag 28 which seals the bag 28 from the outside environment. The bag 28 is sealed along a horizontal section of the bag by the frictional pressure of the ribs exerted against the bag 28 and the folds formed in the bag as a result of the meshing arrangement of the ribs on the crossmembers when the frames are in the closed position. This horizontal seal is adjustable vertically with respect to the bag by the movement of the bag vertically within the frame when in the closed position. Thus, while the bag 28 is securely held in an upright position between the frames 12 and 14, the bag can be slidably moved vertically with respect to the frames 12 and 14 which changes the location of the horizontal seal on the bag, but maintains the sealed condition of the bag. As the bag 28 is slid up or down while engaged between the frames 12 and 14 as desired or necessary during the chromatographic process, the bag remains sealed by the action of the ribs 52 and 54 on the bag.

Alternately, a resilient pad formed of a compressible material may be presented on the inner surface of at least one of the upper crossmembers to provide the seal in the upper end of the bag. The resilient pad will be of a thickness necessary to cause the bag to be sealed by the compression forces of the crossmember against the resilient pad when the frames are in the closed position. Standard weatherstripping is suitable compressible material and can be affixed to the inner surface of the crossmember by known adhesives.

As shown in FIG. 5, a single rib 56 is presented on the inner surface of lower crossmember 18 and a single rib 58 is presented on the inner surface of lower crossmember 19. Ribs 56 and 58 are arranged in an overlapping manner with respect to each other such that when the frames are moved into the closed position a plurality of folds 53 in the lower end of bag 28 are formed. Alternately, the ribs 56 and 58 could be aligned opposite each other on their respective lower crossmembers. These folds 53 provide a seal in the lower end of the bag (in addition to and above the pre-formed seal in the bag 28) and facilitates placing the chromatographic sheet in contact with the liquid solvent in the bag by lowering the position of the chromatographic sheet in the bag when the bag 28 is pulled downward through the apparatus 10. This is accomplished by the user grasping the lower portion of the bag 28 which extends into the space below the lower crossmembers 18 and 19 which causes the chromatographic sheet 32 to come in contact with the liquid solvent in the bag 28. The ribs 56 and 58 extend horizontally substantially the width of the respective lower crossmembers 18 and 19 and can be of any shape or size so long as they are capable of engaging the bag and retaining it in an upright manner between the frames 12 and 14 and provide an airtight seal in the bag. Thus, when a bag 28 is placed between the frames 12 and 14 and the frames are in the closed position, the upper and lower ends of the bag are sealed as described as a result of the action of the ribs 52, 54, 56 and 58. In this arrangement, the bag 28 can be slid vertically with respect to the frames 12 and 14 while maintaining a seal in the upper and lower end of the bag. As the bag 28 is moved up or down, the location of the upper and lower seals move with respect to their position on the bag 28, but the bag remains sealed in an airtight manner.

Typically, in the performance of thin layer chromatography utilizing a bag 28 as the developing chamber, the bag is formed of thin polyethylene tubing such as 0.006 gauge tubing which is sealed at one end to form a bag. The bag is typically longer than the height of the apparatus 10 so that sufficient lengths of the tubing are available to be pulled through the apparatus. A thin layer chromatography development tray 30 holds the chromatographic sheet 32 to which the chemical solution containing the compounds to be identified has been applied. As shown in FIG. 1, a pair of trays 30 can be placed in a back-to-back manner and held together by a clip 34 to provide two chromatographic experiments to be conducted simultaneously within a single bag 28. A saturation pad 36 is placed between the trays 30 to facilitate establishing and maintaining an equilibrium of the solvent vapors in the plastic bag development chamber before and during development of the chromatogram.

There is shown in FIG. 7 an alternative embodiment of the apparatus of the present invention. The apparatus is generally designated by the numeral 100 and comprises a frame 102 formed of an upper crossmember 104, a lower crossmember 106, and a pair of spaced apart, substantially vertical sidewalls 108 and 110 arranged in a manner providing a generally rectangular central opening 112. An upper gate 114 is pivotably connected by a hinge 116 to the upper crossmember 104 and a lower gate 118 is pivotably connected by a hinge 120 to the lower crossmember 106. The lower crossmember 106 and the lower gate 118 are positioned above the distal end of vertical sidewalls 108 and 110 to provide a space below the bottom edge of the lower crossmember 106. A leg 122 is provided extending generally perpendicular to the vertical sidewall 108 and a similar leg 124 is provided extending generally perpendicular from the lower edge of vertical sidewall 110. The legs 122 and 124 cooperate with the leg 126 extending from the lower crossmember 106 to form a stand for maintaining the apparatus 100 in an upright manner. At the end of upper gate 114 opposite the hinge 116, a latch 128 is provided which permits the upper gate 114 to be releasably secured to the upper crossmember 104 when the upper gate 114 is pivoted into the closed position. A similar latch 130 is presented on the end of lower gate 118 opposite hinge 120 to secure the lower gate 118 to the lower crossmember 106 when lower gate 118 is pivoted into the closed position.

As described for the first embodiment of the present invention, three ribs 132 are presented on the inner surface of upper crossmember 104 and two ribs 134 are presented on the inner surface of upper gate 114 for the purpose of providing an air tight seal in a bag inserted between the frame 102 and the gates 114 and 118 when in a closed position. The ribs 134 on the upper gate 114 are arranged in a manner permitting them to mesh with the space between the ribs 132 on upper crossmember 104 to cause a plurality of folds in a bag inserted therebetween. Similarly, a rib 136 is presented on the inner surface of lower crossmember 106 and a rib 138 is presented on the inner surface of lower gate 118 to provide a seal at the lower end of a bag inserted therebetween and to facilitate the movement of solvent in such bag into contact with the chromatography sheet when the bag is pulled downwardly through the frame 102 and gates 114 and 118 when in a closed position.

In use, and with specific reference to the first embodiment of the invention, a chemical solution containing the compound to be identified is spotted onto the chromatography sheet 32 using standard procedures and placed in the tray 30. A saturation pad 36 is placed behind the tray 30 and held thereagainst by a clip 34. A predetermined amount of the desired elution solvent is placed into a bag 28 that already has at least one seal at its lower end. The tray 30 containing the chromatographic sheet 32 is then inserted into the bag 28 to a position above the level of the elution solvent, but permitting the saturation pad to contact the solvent. The bag 28 is then placed against the frame 14 and the frame 12 pivoted to the closed position and secured in the closed position by operation of the latch 38. In this closed position, the bag 28 is held between the frames 12 and 14 by frictional engagement of the bag with the inner surface of the upper crossmembers 16 and 17 and the lower crossmembers 18 and 19. The upper end of the bag is sealed in the manner described by the action of the ribs 52 and 54 and the lower end of the bag is sealed by the action of the ribs 56 and 58. After the bag is inserted into the apparatus 10 and the upper and lower seals engaged, the atmosphere within the bag is permitted to equilibrate. Once the atmosphere has been equilibrated, the bag 28 is pulled downwardly through the apparatus 10 until the solvent level reaches the desired point on the chromatographic sheet 32 to initiate the analysis. When the chromatogram is fully developed, the latch 38 can be released and the frames 12 and 14 pivoted to the open position and the bag 28 removed therefrom. The tray 30 containing the chromatogram on the chromatographic sheet 32 can then be removed from the bag by known techniques for further processing.

While the present invention has been described by reference to specific embodiments, it should be understood that modifications and variations of the invention may be constructed without departing from the scope of the invention as defined in the following claims.

What is claimed is:

1. An apparatus for use in the performance of thin-layer chromatography, a bag sized and dimensioned for developing the chromatogram, the bag having an open upper end and a closed lower end; the apparatus comprising:

a pair of frames each having a pair of spaced apart, substantially vertical sidewalls and spaced apart, substantially horizontal upper and lower crossmembers arranged to form a central opening in each frame, the sidewalls and crossmembers having an inner surface and an outer surface;

hinge means connected between one of the sidewalls of each of the frames for pivoting the frames between an open position and a closed position, the bag being positioned between the frames when in the closed position;

means presented on the inner surface of at least one of the upper crossmembers of the frames for sealably engaging the upper end of the bag positioned between the frames when in the closed position;

means presented on the inner surface of at least one of the lower crossmembers of the frames for sealably engaging the lower end of the bag positioned between the frames when in the closed position; and means for releasably maintaining the frames in the closed position.

2. The apparatus as set forth in claim 1 wherein the sidewalls have an upper end and a lower end, the apparatus further comprising a stand adapted to receive the lower end of the sidewalls in a manner holding the frames in an upright manner when the frames are in the closed position.

3. The apparatus as set forth in claim 2 wherein the frames are substantially identical such that the inner surfaces of the sidewalls and the upper and lower crossmembers of each frame are substantially aligned in a face-to-face relationship when the frames are in the closed position.

4. The apparatus as set forth in claim 3 wherein the means for sealably engaging the upper end of the bag causes the formation of at least one fold in the upper end of the bag.

5. The apparatus as set forth in claim 4 wherein the means for sealably engaging the upper end of the bag comprises at least one rib extending outwardly from the inner surface of each of the upper crossmembers of the frames, the ribs on respective crossmembers being positioned to cause the formation of at least two folds in the upper end of the bag.

6. The application as set forth in claim 5 wherein the upper end of the bag is sealed along a horizontal section of the bag by the frictional engagement of the ribs with the bag and the seal is adjustable vertically with respect to the upper end of the bag by movement of the bag vertically within the frame when in the closed position.

7. The apparatus as set forth in claim 6 wherein the ribs extend horizontally substantially the length of the upper crossmembers.

8. The apparatus as set forth in claim 7 wherein a plurality of spaced apart ribs are presented on the upper crossmember of each of the frames, the ribs being positioned on the respective crossmembers to provide a meshing engagement of at least one rib on one crossmember with the space between a pair of ribs on the corresponding crossmember.

9. The apparatus as set forth in claim 8 wherein each of the plurality of ribs are formed substantially in a straight line.

10. The apparatus as set forth in claim 1 wherein the means for sealably engaging the upper end of the bag comprises a resilient pad presented on and extending outwardly from the inner surface of at least one of the upper crossmembers.

11. The apparatus as set forth in claim 1 wherein the lower crossmember of each frame is positioned above the lower end of the sidewalls of its respective frame to provide a space below the lower crossmembers.

12. The apparatus as set forth in claim 1 wherein the means for sealably engaging the lower end of the bag causes the formation of at least one fold in the lower end of the bag.

13. The apparatus as set forth in claim 12 wherein the means for sealably engaging the lower end of the bag comprises at least one rib extending outwardly from the inner surface of each of the lower crossmembers of the frames, the ribs on respective crossmembers being positioned to cause the formation of at least two folds in the bag.

14. The apparatus as set forth in claim 1 wherein the means for sealably engaging the lower end of the bag comprises a resilient pad presented on and extending outwardly from the inner surface of at least one of the lower crossmembers.

* * * * *